(12) United States Patent
Smit et al.

(10) Patent No.: US 7,966,060 B2
(45) Date of Patent: Jun. 21, 2011

(54) METHOD AND APPARATUS FOR DETERMINING AUTOFLUORESCENCE OF SKIN TISSUE

(75) Inventors: Andries Jan Smit, Groningen (NL); Reindert Graaff, Groningen (NL); Petrus Hendricus N. Oomen, Groningen (NL); Jan Jager, Winschoten (NL)

(73) Assignee: Diagnoptics Holding B.V., Groningen (NL)

( * ) Notice: Subject to any disclaimer, the term of this patent is extended or adjusted under 35 U.S.C. 154(b) by 1396 days.

(21) Appl. No.: 10/767,147

(22) Filed: Jan. 29, 2004

(65) Prior Publication Data

US 2004/0186363 A1 Sep. 23, 2004

Related U.S. Application Data

(63) Continuation of application No. 10/089,575, filed as application No. PCT/NL99/00607 on Sep. 30, 1999, now abandoned.

(51) Int. Cl.
A61B 5/00 (2006.01)
A61B 5/1455 (2006.01)

(52) U.S. Cl. .................................. 600/476; 600/310

(58) Field of Classification Search .................. 600/317, 600/407, 473, 476, 310

See application file for complete search history.

(56) References Cited

U.S. PATENT DOCUMENTS

| | | | |
|---|---|---|---|
| 4,773,722 A | 9/1988 | Perino | |
| 5,279,297 A | 1/1994 | Wilson et al. | |
| 5,452,723 A | 9/1995 | Wu et al. | |
| 5,601,079 A | 2/1997 | Wong et al. | |
| 5,755,226 A * | 5/1998 | Carim et al. | 600/323 |
| 5,851,181 A | 12/1998 | Talmor | |
| 6,436,127 B1 | 8/2002 | Anderson et al. | |
| 6,505,059 B1 | 1/2003 | Kollias et al. | |
| 6,721,582 B2 | 4/2004 | Trepagnier et al. | |
| 2006/0195022 A1 | 8/2006 | Trepagnier et al. | |

FOREIGN PATENT DOCUMENTS

| | | |
|---|---|---|
| DE | 37 18202 C1 | 11/1988 |
| EP | 0 003 015 | 7/1979 |
| WO | 97/15226 | 5/1997 |

OTHER PUBLICATIONS

M.H. Dominiczak et al., *Increased Collagen-Linked Fluorescence in Skin of Young Patients With Type 1 Diabetes Mellitus*, Diabetes Care, May 1990, vol. 13, No. 5, pp. 468-472.

P.J. Beisswenger et al., *Formation of Immunochemical Advanced Glycosylation End Products Precedes and Correlates With Early Manifestations of Renal and Retinal Disease in Diabetes*, Diabetes, Jul. 1995, vol. 44, pp. 824-829.

M. Brownlee, *Glycation and Diabetic Complications*, Diabetes, Jun. 1994, vol. 43, pp. 836-841.

D.R. Sell et al., *Pentosidine Formation in Skin Correlates With Severity of Complications in Individuals With Long-Standing IDDM*, Diabetes, Oct. 1992, vol. 41, pp. 1286-1291.

R.H. Nagaraj et al., *Evidence of a Glycemic Threshold for the Formation fo Pentosidine in Diabetic Dog Lens but Not in Collagen*, Diabetes, May 1996, vol. 45, pp. 587-594.

R.H. Mayer et al., *Measurement of the fluorescence lifetime in scattering media by frequency-domain photon migration*, Applied Optics, Aug. 1999, vol. 38, No. 22, pp. 4930-4938.

* cited by examiner

*Primary Examiner* — Eric F Winakur
(74) *Attorney, Agent, or Firm* — Pearne & Gordon LLP

(57) ABSTRACT

For determining autofluorescence of a clinically normal skin issue (7) of a patient, the tissue (7) is irradiated with electromagnetic radiation. An amount of fluorescent radiation emitted by the tissue (7) in response to the irradiation is measured and, in response thereto, a signal is generated which represents a determined autofluorescence in agreement with the measured amount of electromagnetic radiation. Because the tissue (7) is skin tissue (7) in vivo and irradiation is performed noninvasively, a method which is very simple to apply for determining autofluorescence is obtained. An apparatus especially adapted for use in this method is also described.

20 Claims, 2 Drawing Sheets

METHOD AND APPARATUS FOR DETERMINING AUTOFLUORESCENCE OF SKIN TISSUE

This application is a continuation application of U.S. patent application Ser. No. 10/089,575, which was the U.S. national phase patent application of PCT/NL99/00607, filed Sep. 30, 1999.

This application was published in English on Apr. 5, 2001 as International Publication Number WO 01/22869.

TECHNICAL FIELD

This invention relates to a method and an apparatus for determining an autofluorescence value of clinically healthy skin tissue. It is supposed that autofluorescence of clinically healthy skin tissue can serve as an indication for an AGE content in a tissue of a patient. This involves measuring the extent to which a portion of the tissue exhibits fluorescence upon excitation with light and/or with radiation in a wavelength region near the visible region.

BACKGROUND OF THE PRIOR ART

Studies have shown there is a relation between the occurrence of complications in diabetes mellitus patients and the amount of native fluorescence, or autofluorescence, of the eye lens and of skin biopsies. Reference is made to, for instance, Sell, D. R. et al., *Pentosidine formation in skin correlates with severity of complications in individuals with long-standing IDDM*, Diabetes 1992; 41:1286-92.

According to the current insights, this relation is attributed to the presence of so-called AGE's (advanced glycation/glycosylation end products), such as pentosidine. In patients with diabetes mellitus, the AGE level in the skin proves to correlate accurately with preclinical nephropathy and early retinopathy. AGE's are substances originating from irreversible glycoxidation reactions of glucose with amino acid groups of proteins. An example is the pentosidine referred to, which consists of a crosslink between lysine and arginine. The formation of irreversible glycation products on proteins may interfere with the function of such proteins. Formation of AGE's on the collagen of the vascular wall may lead to structural changes, such as less elastic blood vessels. Especially for long-lived structural proteins, such as collagen and elastin, it is of importance that the formation of AGE's proceeds slowly.

The AGE level increases with age, but in healthy people this increase is considerably smaller than in patients with diabetes mellitus.

A method as set forth in the introductory part of claim 1 is known from Marek, H. et al, *Increased Collagen-Linked Fluorescence in Skin of Young Patients With Type I Diabetes Mellitus*, Diabetes 1990; 5:468-472. In it, the autofluorescence value is determined ex vivo by exciting suspension preparations obtained from material of a skin tissue biopsy. By measuring the native fluorescence of that skin material, the AGE level in a person to be examined can, at least supposedly so, be determined, and it is possible to make predictions about the chances of complications in diabetes.

In this known method, by incision with local anesthesia, a biopsy of clinically normal skin of the buttock is taken. The biopsies are deep-frozen until they are analyzed. Prior to analysis, the skin samples are defrosted and subcutaneous fat is scraped off the skin samples. The residual tissue is washed in a 0.15 M saline solution, dried with filter paper and weighed. Thereafter, selected samples are subjected to homogenization, washing and lipid extraction. The autofluorescence of a thus obtained suspension of the tissue material is measured. For that matter, it has also been previously described that AGE levels in the tissue material of skin biopsies can be determined in ways other than by measurement of autofluorescence.

Drawbacks of this method of determining autofluorescence are that it is necessary to take biopsies from the skin of a patient, that the processing of the skin material for measuring autofluorescence is laborious and time consuming, and that a long period of time elapses between the time when a biopsy is taken and the time when the measuring results become available, so that these results cannot be communicated directly to the patient, which necessitates separate communication to that effect.

The object of the invention is to provide a solution which enables the autofluorescence of skin tissue of patients to be measured in a simpler manner, whereby nonetheless a sufficiently reliable measuring result is obtained.

SUMMARY OF THE INVENTION

To achieve the above-mentioned object, the invention provides a method according to claim 1. The invention further provides an apparatus according to claim 17, which is specifically suitable for carrying out the proposed method.

By irradiating a portion of the skin tissue in vivo and carrying out the irradiation noninvasively, a measurement of the autofluorescence of the skin tissue is obtained which can serve as a measure for the AGE content (and possibly also for a potential other underlying explanation for the relation between autofluorescence and diabetes mellitus or possible other disorders, such as renal or hepatic deficiency), without requiring that skin samples be taken and processed to form a homogenized suspension.

This is despite the fact that in irradiating the skin a part of the radiation is reflected on the skin surface, another part of the radiation, though it penetrates the skin, is absorbed there or, after being scattered in the tissue, exits again, and thus only a small part of the radiation directed at the skin leads to fluorescent radiation. Incidentally, of the fluorescent radiation too, a portion is absorbed in the skin, while the skin tissue in vivo has not been brought into a normalized, homogenized condition as is the case in the known measuring technique. The method and the apparatus according to the present invention nonetheless enable determination of the weak fluorescence from the intact, in vivo skin tissue, which can serve as a measure for AGE contents.

It is noted that methods and apparatuses for determining autofluorescence of skin tissue in vivo are known per se, for instance from German patent application 37 18 202. However, that involves the identification of abnormal differences in autofluorescence between different portions of the skin as a result of diseases of the skin, in particular as a result of cancer. There is a considerable difference in skin fluorescence between healthy tissue and tumor tissue, and therefore tumor tissue can be detected by analysis of the long-wave spectrum which, upon irradiation of ultraviolet light, is emitted through fluorescence in the skin. The accurate determination of the size of the tumor tissue is important there.

In the application of the method and apparatus according to the invention, by contrast, it is the autofluorescence of the clinically healthy skin that is determined. This involves the determination of a general autofluorescence value which is individual-specific and holds for non-locally anomalous skin tissue. Measurement is done on skin tissue which may be assumed a priori to be clinically healthy and not to exhibit any autofluorescence essentially different from the autofluorescence of most other parts of the skin tissue of the patient. Locally anomalous skin tissue, such as nevi, warts, scars, skin tissue affected by sunburn, tattoos and very hairy skin tissue, is avoided as much as possible and not separately measured.

Further objects, aspects, effects and details of the invention are explained in the following in and by the description, with reference to the drawings.

DETAILED DESCRIPTION

Figure 1:
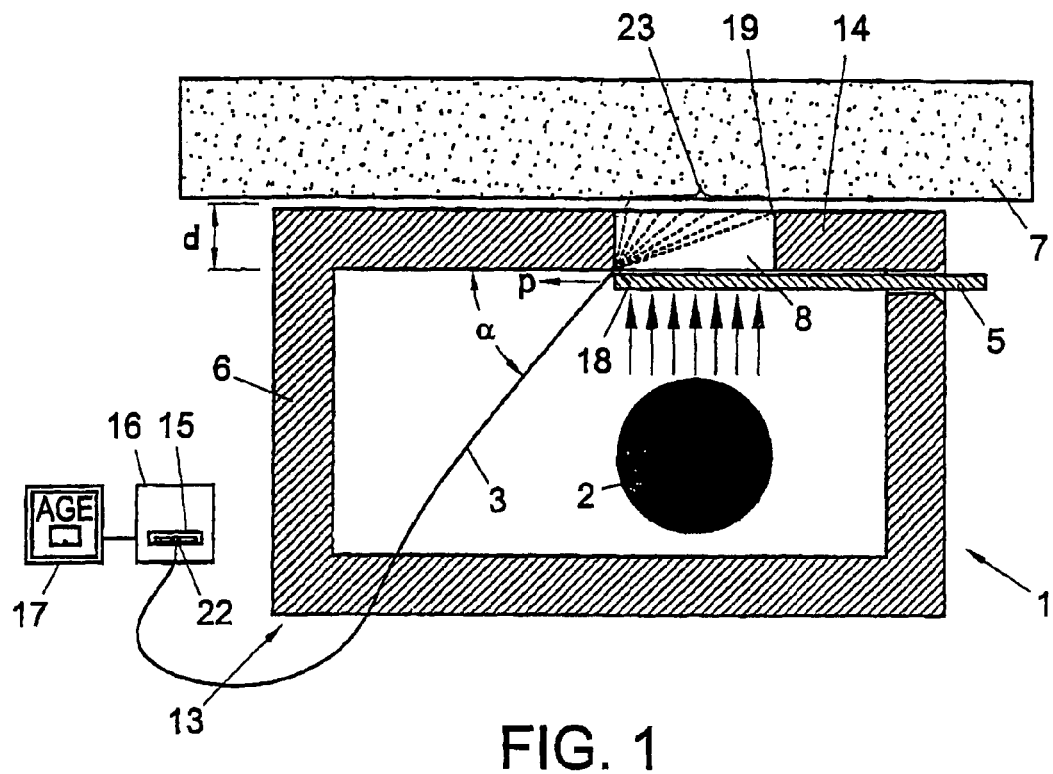
FIG. 1 is a diagrammatic representation in cross-section of an exemplary embodiment of an apparatus according to the invention.

The measuring system 1 shown in FIG. 1, for measuring an AGE content in a tissue of a patient, constitutes a currently most preferred exemplary embodiment of the invention. The measuring system 1 according to this example comprises a measuring unit 13 having as a light source a fluorescent lamp in the form of a blacklight fluorescent tube 2, which is arranged within a supporting structure in the form of a light-shielding casing 6. The casing 6 has a contact surface 14 which is placed against the skin 7. An opening in the contact surface 14 forms an irradiation window 8 through which a portion of the surface of the skin 7 located behind that irradiation window 8 and adjacent to the window opening, can be irradiated.

To provide that, of the radiation generated by the fluorescent tube, only UV light in the desired wavelength range reaches the skin 7, there is placed, according to this example, a filter 5 in front of the irradiation window 8. Such filters may be adapted, for instance, for passing radiation in a wavelength band around a desired wavelength in the range of 300 to 420 nm or may be high-pass filters for passing light radiation in a wavelength band from, for instance, 320, 375, 385 or 395 nm. The upper limit of the wavelength spectrum reaching the skin is then determined by the upper limit of the wavelength range of the light emitted by the proposed blacklight fluorescent tube (in this example 420 nm). Suitable filter types are, for instance, the 2 mm filters WG320, GG375, GG385 and GG395 of Schott Glaswerke, Mainz, Germany. In principle, the irradiation window 8 may also be formed by a fully open passage. Further, the irradiation window may be of a rectangular, circular or different shape.

In response to the radiation reaching the skin, the skin 7 emits radiation which passes back through the irradiation window 8. The greater part of that radiation has a wavelength in the wavelength range of the radiation sent to the skin. A part of the radiation sent back via the irradiation window, however, is formed by radiation having longer wavelengths, which is generated as a result of a fluorescent action of constituents of the skin in response to excitation by the light sent to the skin.

Located adjacent an edge of the irradiation window 8 is an end 18 of an optical fiber 3, which end forms a measuring window 18 via which radiation to be detected, coming from the skin, is passed to a detector. The optical fiber 3 passes the radiation received via the measuring window 18 to a spectrophotometer unit 15 with an array 22 of detectors. A suitable type of optical fiber is, for instance, a 200/250 μm glass fiber of a length of 1 m and with FSMA connectors. The spectrometer is designed as a digitally computer-readable plug-in card in a standard computer 16. A suitable type is, for instance, the PC 1000 van Ocean Optics with a sampling frequency of 10 kHz. Such a spectrometer analyzes the optical spectrum into a large number of fractions (in this example 1100 fractions in the range between 233 and 797 nm), which data can be further analyzed by means of the computer 16. The computer 16 is programmed with a program for generating signals representing an AGE content in the skin 7 on a display 17.

The detector array 22 is adapted for separately measuring radiation coming from the irradiated portion of the skin 7, firstly in a wavelength range outside the wavelength range of the radiation with which the skin 7 is irradiated and, secondly, in a wavelength range within or equal to the wavelength range of the radiation with which the skin 7 is irradiated. The measurement in a wavelength range within or equal to the wavelength range of the radiation with which the skin 7 or a reference material is irradiated serves to normalize for the amount of light emitted by the lamp and for optical properties of the skin tissue of the patient.

The amount of electromagnetic radiation emitted by the skin tissue 7 in response to the irradiation, in a wavelength range outside the wavelength range of the radiation applied to the skin 7 is measured by means of the detector array 22. The spectrometer generates a digital signal which is fed to the computer 16. Software loaded into the computer then provides, by means of the display 17, for the generation of a signal which represents a measured autofluorescence in agreement with the measured amount of electromagnetic radiation in the wavelength range outside the wavelength range of the radiation applied to the skin 7. According to this example, the software is further designed for optionally processing the amount of electromagnetic radiation, measured via measuring window 18, in the wavelength range within the wavelength range of the radiation applied to the skin 7, for the purpose of correcting for the optical properties of the skin tissue.

The signal which represents a measured autofluorescence is subsequently converted to a signal which represents an AGE content and which may be in the form of, for instance, a number shown, which represents the determined content of AGE's, but may also be in the form of, for instance, an index number shown, which represents a value relative to an average AGE value for the age of the patient in question. Also, for instance, positions on a scale may be indicated, so that, along with the measured value, a reference framework is furnished at the same time.

It is noted that the use of a spectrometer provides the advantage that it can be accurately determined per narrow wavelength band to what extent it is being taken into account as an indicator of the presence of AGE's.

The irradiation window 8 is bounded by an edge 19 to be held against a skin of a patient and thus limits the skin surface to be irradiated. The measuring window 18 too has a particular surface for passing light to be detected coming from the irradiated portion of the skin tissue 7. The irradiation window 8 and the measuring window 18 each have a passage surface, the passage surface of the irradiation window 8 being greater than the passage surface of the measuring window 18. Further, the surface 23 of the skin 7 within the irradiation window 8 from where light can be received by the fiber via the measuring window 18 is preferably greater than 0.1 $cm^2$ and in particular 1-4 cm$^2$, but smaller than the irradiation window and hence smaller than the irradiated surface of the skin 7.

The surface 23 of the skin 7 within the irradiation window 8 from where light can be received via the measuring window 18 is further preferably greater, and in particular preferably at least 3-20 times greater, than the measuring window, so that a large irradiated and measured skin surface is combined with a compact construction of the measuring it.

Inasmuch as the skin surface irradiated simultaneously in operation is relatively large and the radiation in response thereto stemming from different portions of that skin surface is detected in mutual simultaneity, different effects are achieved which are of particular advantage in determining an AGE content of skin tissue which is representative of a particular patient. The skin surface to be measured is then preferably at least about 0.1 cm$^2$ and in particular preferably 1 to 4 cm$^2$.

In the first place, measurement thus involves an averaging of radiation coming from a large skin surface, so that a possible influence of local differences in skin properties on the detected fluorescence of the skin tissue is eliminated.

In the second place, what is achieved by the use of a large irradiation window and measuring a large skin surface 23 is that a considerable portion of fluorescent radiation which has been scattered further by the skin before exiting is received as well, so that the proportion of fluorescent radiation with respect to light reflected from the surface of the skin is increased.

Thirdly, a large skin surface can be properly irradiated with a fluorescent lamp Relatively much radiation energy of the fluorescent tube is emitted in a wavelength range of 300-420 nm. As a result, a large portion of the emitted radiation is sent to the skin and only little radiation is absorbed by the casing 6. Accordingly, relatively much fluorescence is generated without the skin being locally subject to strong heating, which might be painful and entail skin burning phenomena or at least an increased chance of artifacts as a result of reactions of the skin, such as modifications in the blood supply (vasodilatation).

Further, the optical filter 5 located between the radiation source 2 and the skin 7 passes substantially exclusively radiation which serves for exciting fluorescence.

The measuring window 18 formed by the end of the optical fiber 3 proximal to the skin 7 is oriented at an angle α a of about 45° relative to the irradiation window 8. As a result, in use the measuring window 18 is held at an angle of about 45° relative to the irradiated surface of the skin 7.

The position of the measuring window 18 at an angle of 25-65° and preferably at an angle of about 45° relative to the irradiated surface of the skin 7 is advantageous, because radiation reflected by the surface of the skin 7 by mirror reflection, which is not of interest in this context, is reflected relatively strongly in a direction perpendicular to the skin surface. Thus, owing to the inclined position of the measuring window, relatively little radiation reflected mirror-wise by the surface of the skin 7 is received.

Owing to the inclined position of the measuring window, further, the distribution of the proportion of the light received from different zones of the irradiated skin surface is more uniform than in the use of a measuring window parallel to the irradiation window. In particular, overrepresentation of radiation coming from a portion of the irradiated skin surface closest to the measuring window 18 is prevented.

An advantage of the inclined position of the measuring window 18 that holds in particular if the skin 7 is irradiated in a direction perpendicular thereto is that the measuring window 18 is not directed in a direction in which it casts a shadow.

By moreover placing the measuring window 18 at an edge of the irradiation window 8, the attachment thereof is simplified, and what is prevented, further, is that the measuring window 18, and a part of the optical fiber 3 adjacent thereto, are situated in the path of radiation between the lamp 2 and the portion of the skin 7 to be irradiated.

As appears from FIG. 1, the measuring window 18 is spaced from the passage surface of the irradiation window 8, so that in use the measuring window 18 is held at a distance d from the skin 7. A suitable distance d is, for instance, 5-9 mm. In the example described, the distance d is approximately 7 mm. A suitable guideline for the distance d is further that it be selected such that the middle of the measuring window 18 is directed at a central area of the irradiation window 8. Given a position of the measuring window 18 at an angle of 45° relative to a plane in which the irradiation window 8 extends, and placement of the measuring window in front of an edge of the irradiation window 8, the distance d according to that guideline is half of the transverse dimension of the irradiation window 8 in a direction of the directional component parallel to the irradiation window 8 in which the measuring window 18 is directed. In practice, such a distance gives a suitable distribution of the yield of fluorescent radiation coming from the skin 7 over zones at different depths from the skin surface.

According to this example, the lamp is a blacklight fluorescent tube having a wavelength range of λA 300-420 nm. Such a UV lamp has a bandwidth such that by changing the optical filter 5 autofluorescence measurements at different excitation wavelengths can be readily carried out.

Figure 2:
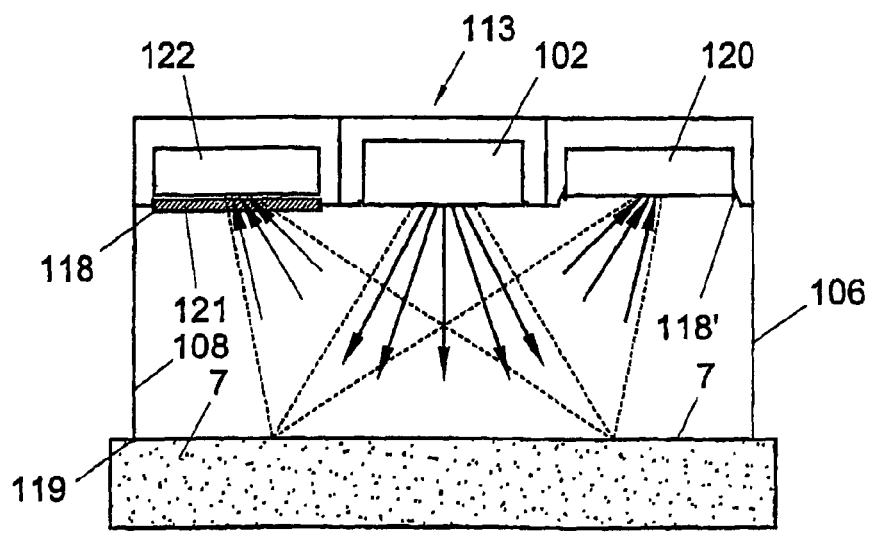
FIG. 2 is diagrammatic representation of a measuring unit of a system according to a second exemplary embodiment of the invention.

In the considerably smaller measuring unit 113 shown in FIG. 2, as radiation source a LED 102 is used which, according to this example, emits radiation of a wavelength of 370 nm. Because the measuring unit 113 is designed as a compact measuring head, it can simply be held against a patient's body at different points. A LED of a wavelength in the range of λA 300-420 nm emits light of a narrow band (width at half of the highest intensity, for instance, 10 nm), so that no or little radiation outside the desired wavelength range is emitted and correspondingly little energy leads to heat development. LED's moreover are highly efficient light sources and therefore remain relatively cool themselves too. Further, LED's are easy to control in a pulsed or modulated fashion, which is advantageous for correcting, for instance, for dark current due to the detector 122 or ambient light. The measuring unit 113 has a screening 106 and an irradiation window 108 having a limiting edge 119 to be placed against the skin 7.

For detecting radiation coming from the skin 7, two detectors 120, 122 are used which simultaneously detect radiation coming from the skin 7. Arranged between the detector 122 and the skin 7 is a long pass filter 121, which passes only radiation of a wavelength greater than, for instance, 400 nm, so that the detector 122 only detects the fluorescence-induced radiation passing the window 118. The detector 120 detects the total amount of light coming from the skin 7 and passing the window 118'.

By measuring not only the fluorescence-induced longwave radiation, but also the radiation coming from the skin 7 in the wavelength range of the excitation radiation, as in FIG. 2 with the detector 120, a correction can be made for differences in intensity of the radiation source and differences in optical properties of the skin 7 by carrying out the generation of the AGE content signal partly in accordance with the amount of detected electromagnetic radiation in the wavelength range of the excitation radiation.

By measuring with two detectors, the ratio between measured intensities solely in the wavelength range of the fluorescence and of radiation over the totality of wavelengths can then be simply determined. In principle, such a ratio can also be determined with, for instance, a single detector and a chopper which passes alternately radiation of all wavelengths and radiation solely above a particular wavelength. This provides the advantage that measuring errors as a result of differences between the two detectors are prevented, but leads to an increase of the dimensions and the mechanical complexity of the measuring unit. It appears, incidentally, that the ratio between the intensity of the autofluorescence and the intensity of the total amount of light reflected and emitted by the skin is about 1%.

It may be advantageous to have several LED's and/or laser diode sources excite sequentially at different wavelengths and to measure the autofluorescence obtained upon excitation at those different wavelengths.

Another option is to use a LED or laser diode which emits radiation in the region of the fluorescence generated. Thus, the reflection can also be measured at the wavelengths of the generated fluorescence, which provides information about the optical properties of the skin tissue and hence the propagation behavior of light of those wavelengths through the skin tissue. This information can subsequently be used for correcting measuring results for differences in optical properties of the skin as regards propagation properties of light of the wavelengths generated by fluorescence.

For each wavelength range, several detectors can be used which are placed at different distances from the skin and (parallel to the skin) from the radiation source for simultaneously measuring radiation with different distributions of contributions from different depth zones of the skin.

For the accuracy of the determination of AGE contents, if there is simultaneous irradiation with all excitation wavelengths used and also the fluorescent radiation is detected simultaneously, it is favorable if all wavelengths of the wavelength range of the excitation radiation are lower than all wavelengths of the wavelength range in which fluorescent radiation is measured. The wavelength range of the excitation radiation preferably includes at least one wavelength in a range of 300-420 nm and the wavelength range in which fluorescent radiation is measured preferably includes at least one wavelength in a range $\leq 600$ nm.

For the accuracy of the determination of AGE contents, it is further favorable if over the wavelength range in which fluorescent radiation is measured the aggregated, for instance summed, amount of detected fluorescent radiation is measured, and the generation of the signal occurs in accordance with the aggregated amount of detected fluorescent radiation. The fact is that because the excitation and emission bands of different specific types of AGE's present in the patient may overlap, fluorescence may occur at several wavelengths, so that a spectrum is emitted having a wideband long-wave region in the range of about 420-600 nm. By measuring over such a wideband long-wave region, autofluorescence owing to these effects is also taken into account.

To be able to accurately measure the accuracy of the weak autofluorescence as a result of the presence of AGE's over a longer time as well, it is advantageous to regularly carry out a reference measurement on a reference material, and to have the generation of the AGE content signal partly influenced by an amount of electromagnetic radiation detected in the reference measurement.

It is also possible to carry out the measurement with a detector which measures the response to excitation light after the irradiation with excitation light (for instance with a light pulse) has been stopped or at least has been changed, for instance in intensity. The fact is that the light coming from the skin in response to excitation light initially consists of light with the reflected excitation light and thereafter contains fluorescent light exponentially decreasing in strength. Thus, the extent to which changes in light coming from the skin lag behind changes in the excitation light also forms a measure for the autofluorescence. The skin surface can be irradiated with, for instance, pulsed or modulated light, utilizing a delay or phase lag of light received from the skin in response thereto as a measure for the autofluorescence value. Instead of, or supplemental to, the change of the intensity of the excitation light, also the wavelength of the excitation light can be changed, while changes in the light coming from the skin in response to changes in the wavelength of the excitation light serve as a measure for the autofluorescence. At different wavelengths, for instance, different AGE's can be excited and emit fluorescent light.

For determining the AGE content, both the measurements at different times and the half value of the response signal can then be used as an indication. An example of measuring the response to modulated excitation light is described in more detail in R. H. Mayer et al., *Measurement Of The Fluorescence Lifetime In Scattering Media By Frequency Domain Migration*, Applied Optics, August 1999, pp. 4930-4938, which is hereby referred to.

An advantage of the consecutive irradiation of skin tissue and subsequent measurement of fluorescence is that the wavelengths of the fluorescent light and of the excitation light can overlap without this disturbing the measurement.

The consecutive irradiation and measurement of fluorescence can be achieved, for instance, by having the LED or laser diode 102 in FIG. 2 radiate in a pulsatile manner and carrying out the measurement with the detector 120—the detector 122 and the filter 121 can then be omitted—in alternation with the irradiation, so that measurement takes place when the LED or laser diode 102 emits no light, or at least a different amount of light. Incidentally, it is also possible to measure fluorescence both simultaneously with excitation and after changes in the excitation light. The distinction between reflected excitation light and fluorescent light is then made on the one hand on the basis of a difference in wavelength and on the other on the basis of the delay by which fluorescent light is emitted.

Figure 3:
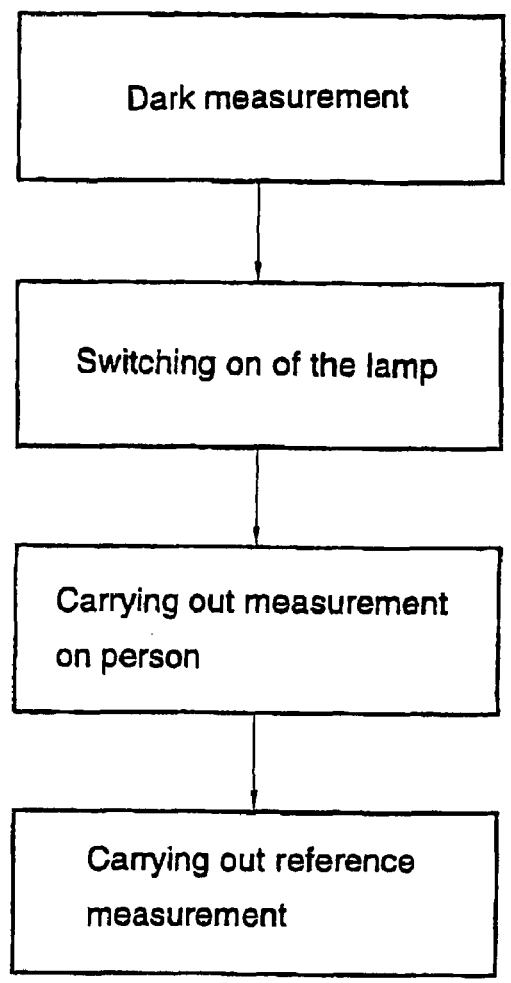
FIG. 3 is a diagram of an example of a method according to the invention.

Hereinafter, a tested method for determining the autofluorescence in the skin is described in more detail. A measuring system according to FIG. 1 was used. The steps of this method are schematically represented in FIG. 3.

First, a dark measurement is carried out by measuring the dark current of the detector when the opening is covered, without light irradiation. The temperature of the spectrograph is subsequently maintained constant to prevent variation of the dark current.

Next, the blacklight fluorescent tube 2 is turned on, followed by waiting for some time (for instance at least 5 minutes) until the tube 2 generates a substantially constant light output.

Thereafter, the measuring unit 13 is placed on the skin 7 of a person to be examined. This can be, for instance, a part of the lower arm or of the leg (such as the calf). A measurement is performed, and the spectral intensity distribution of radiation coming from the skin 7 as determined by the spectrometer is stored in the computer 16.

Thereafter, a reference measurement is performed, by performing the same measurement on a reference material, for instance white Teflon. This may also be done prior to the preceding step.

Performing the reference measurement serves to enable correction for differences in the amount of absorption and scattering that occur between different test subjects. The amount of absorption is associated inter alia with age, the melanin content of the skin tissue, and the amount of blood in the skin.

Figure 4:
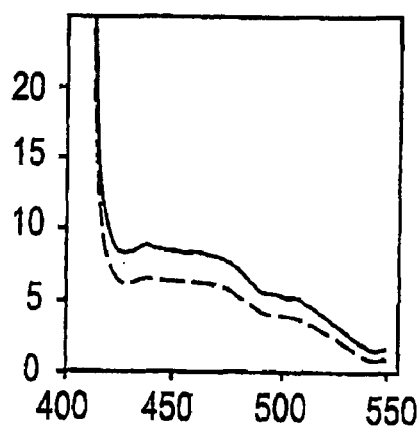
FIG. 4 is an example of a normalized spectrogram of light intensities observed in the measured wavelength range.

FIG. 4 shows a result of the autofluorescence measured in diabetic patients (solid line) and a healthy control group corresponding in age and gender (dotted line). The diagram has been normalized by dividing the measured intensities by the sum of the intensities measured between 285 and 425 nm. It is clear to see that over the measured region between 400 and 500 nm, the autofluorescence in the diabetics is essentially higher, which is consistent with results achieved heretofore using other, more laborious measuring techniques.

The registered measurements further confirm that an important measure for autofluorescence is the aggregated light intensity AFt in the range of 420-600 nm. Diabetic patients (both with and without correction for absorption) proved to have a considerably higher fluorescence level than healthy individuals.

This is represented in the following table (arbitrary units):

| AFt $_{420-600\ nm}$ | Diabetics (n = 46) | Control (n = 46) | Statistic significance |
|---|---|---|---|
| lower arm | 1598 ± 703 | 1184 ± 618 | p < 0.004 |
| lower leg | 1637 ± 923 | 1255 ± 847 | p < 0.04 |

The measuring values found, corrected for absorption, also prove to correlate with age (r=0.52; p<0.001, where r represents the correlation coefficient between the measured autofluorescence and age, and p represents the level of statistical significance of the correlation). The two groups of test subjects had ages distributed over a wide range. Thus, upon a comparison by age, still greater differences are found. In all of the 46 pairs matched for age and gender, a higher AFt was found in the diabetic patient than in the control.

The measuring values found, corrected for absorption, moreover prove to correlate with the amount of laboratory-determined values for HbA1c (r=0.4; p<0.01, where r is the correlation coefficient between the measured autofluorescence and the measured HbA1c value—a frequently used measure for long-term glucose levels).

It appears from these data that the clinically significant indications of the AGE values of skin tissue can be determined in the noninvasive manner according to the invention.

It will be clear to those skilled in the art that within the framework of the invention many other embodiments and modes are possible and that the invention is not limited to the examples described hereinbefore.

The invention claimed is:

1. A method for determining an advanced glycation/glycosylation end product content of non-locally anomalous, intact skin tissue of a human individual, comprising:
using a radiation source to irradiate said skin tissue with electromagnetic excitation radiation;
receiving and measuring an amount of electromagnetic, fluorescent radiation emitted by said skin tissue in response to said irradiation; and
generating, in response to said measured amount of fluorescent radiation, a signal which represents said measured amount of fluorescent radiation; and
determining an advanced glycation/glycosylation end product content of said skin tissue from said signal, and outputting said determined advanced glycation/glycosylation end product content;
wherein said skin tissue is non-locally anomalous, intact skin tissue in vivo which is irradiated noninvasively and simultaneously in its entirety by directing said radiation from said radiation source to a portion of the outer surface of the skin, wherein fluorescent radiation emitted in response to said irradiation is simultaneously received from a surface area of the irradiated portions of the skin surface of at least 1 cm$^2$, wherein said fluorescent radiation is received via a measuring window; and wherein said measuring window is oriented at an angle of 25-65° relative to the irradiated portion of the surface of the skin.

2. A method for determining an advanced glycation/glycosylation end product content of non-locally anomalous, intact skin tissue of a human individual, comprising:
using a radiation source to irradiate said skin tissue with electromagnetic excitation radiation;
receiving and measuring an amount of electromagnetic, fluorescent radiation emitted by said skin tissue in response to said irradiation; and
generating, in response to said measured amount of fluorescent radiation, a signal which represents said measured amount of fluorescent radiation; and
determining an advanced glycation/glycosylation end product content of said skin tissue from said signal, and outputting said determined advanced glycation/glycosylation end product content;
wherein said skin tissue is non-locally anomalous, intact skin tissue in vivo which is irradiated noninvasively and simultaneously in its entirety by directing said radiation from said radiation source to a portion of the outer surface of the skin, wherein fluorescent radiation emitted in response to said irradiation is simultaneously received from a surface area of the irradiated portions of the skin surface of at least 1 cm$^2$, wherein a supporting structure is held against the skin of the individual, wherein the irradiated skin tissue area is located behind an opening in the supporting structure, wherein the supporting structure supports a measuring window, wherein said fluorescent radiation is received via said measuring window and wherein said measuring window is held at a distance from the skin.

3. An apparatus for determining an advanced glycation/glycosylation end product content of non-locally anomalous, intact skin tissue of a human individual, comprising:
a pick-up unit with:
a radiation source, for in vivo and noninvasively irradiating a surface portion of intact skin tissue behind an irradiation window with electromagnetic excitation radiation; and
a detector for measuring an amount of electromagnetic fluorescent radiation received from only a portion of said irradiated skin surface portion;
circuitry connected to said pick-up unit for generating an autofluorescence value for said non-locally anomalous, intact skin tissue in agreement with the measured amount of fluorescent radiation, for determining an advanced glycation/glycosylation end product content of said skin tissue from said signal, and for outputting said determined advanced glycation/glycosylation end product content; and
a measuring window bounding a surface area for passing fluorescent radiation to be detected from said portion of the skin surface from which said amount of fluorescent radiation is received to the detector, said portion of the skin surface from which said amount of fluorescent radiation is received being larger than the surface area bounded by said measuring window.

4. An apparatus according to claim 3, wherein said portion of the skin surface from which said amount of fluorescent radiation is received is at least three times larger than the surface area of said measuring window.

5. An apparatus for determining an advanced glycation/glycosylation end product content of non-locally anomalous, intact skin tissue of a human individual, comprising:
a pick-up unit with:
a radiation source, for in vivo and noninvasively irradiating intact skin tissue behind an irradiation window with electromagnetic excitation radiation by directing said radiation from said radiation source to a portion to be irradiated of the outer skin surface; and
a detector for measuring an amount of electromagnetic fluorescent radiation simultaneously received from a surface area of the irradiated portion of the skin surface of at least 1 $cm^2$; and
circuitry connected to said pick-up unit for generating an autofluorescence value for said non-locally anomalous, intact skin tissue in agreement with the measured amount of fluorescent radiation originating from said surface area of said skin tissue, for determining an advanced glycation/glycosylation end product content of said skin tissue from said signal, and for outputting said determined advanced glycation/glycosylation end product content, further comprising a supporting structure to beheld against the skin of the individual, for defining a plane in which a surface portion of said skin tissue to be irradiated is located, wherein the supporting structure supports a measuring window for passing light to be detected originating from said irradiated skin tissue, said measuring window being oriented at an angle of 25-65° relative to said plane and located for receiving radiation emitted from the skin in a direction at an angle to the direction of the excitation radiation.

6. An apparatus according to claim 5, wherein said supporting structure comprises the irradiation window, said measuring window being located adjacent an edge of said irradiation window.

7. An apparatus for determining an advanced glycation/glycosylation end product content of non-locally anomalous, intact skin tissue of a human individual, comprising:
a pick-up unit with:
a radiation source, for in vivo and noninvasively irradiating intact skin tissue behind an irradiation window with electromagnetic excitation radiation by directing said radiation from said radiation source to a portion to be irradiated of the outer skin surface; and
a detector for measuring an amount of electromagnetic fluorescent radiation simultaneously received from a surface area of the irradiated portion of the skin surface of at least 1 $cm^2$; and
circuitry connected to said pick-up unit for generating an autofluorescence value for said non-locally anomalous, intact skin tissue in agreement with the measured amount of fluorescent radiation originating from said surface area of said skin tissue, for determining an advanced glycation/glycosylation end product content of said skin tissue from said signal, and for outputting said determined advanced glycation/glycosylation end product content, further comprising a supporting structure to be held against the skin of the individual, for defining a plane in which a surface of said skin tissue to be irradiated is located behind an opening in the supporting structure, wherein the supporting structure supports a measuring window for passing light to be detected originating from said irradiated skin tissue, wherein said measuring window is spaced away from said plane.

8. A method for determining an advanced glycation/glycosylation end product content of non-locally anomalous, intact skin tissue of a human individual, comprising:
using a radiation source to irradiate said skin tissue with electromagnetic excitation radiation;
receiving and measuring an amount of electromagnetic, fluorescent radiation emitted by said skin tissue in response to said irradiation; and
generating, in response to said measured amount of fluorescent radiation, a signal which represents said measured amount of fluorescent radiation; and
determining an advanced glycation/glycosylation end product content of said skin tissue from said signal, and outputting said determined advanced glycation/glycosylation end product content;
wherein said irradiated skin tissue is non-locally anomalous, intact skin tissue in vivo which is irradiated noninvasively and simultaneously in its entirety by directing said radiation from said radiation source to a portion of the outer surface of the skin, wherein the measured fluorescent radiation emitted in response to said irradiation is simultaneously received from only a portion of said irradiated portion of said skin surface.

9. A method according to claim 8, wherein the measured fluorescent radiation is received via a measuring window bounding a surface area, and wherein said portion of the irradiated portion of the skin surface from which the measured fluorescent radiation is received has a surface area larger than the surface area bounded by said measuring window.

10. A method according to claim 9, wherein the surface area of the skin from which the measured fluorescent radiation is received is at least three times larger than the surface area bounded by said measuring window.

11. A method according to claim 8, wherein the measured fluorescent radiation has one or more wavelengths larger than 420 nm.

12. A method according to claim 8, wherein the size of the portion of the irradiated skin surface portion from which the measured fluorescent radiation is received is at least 1 $cm^2$.

13. A method according to claim 8, wherein the fluorescent radiation emitted in response to said irradiation is simultaneously received from a surface area of the irradiated portion of the skin surface larger than 0.1 $cm^2$.

14. An apparatus for determining an advanced glycation/glycosylation end product content of non-locally anomalous, intact skin tissue of a human individual, comprising:
a pick-up unit with:
a radiation source, for in vivo and noninvasively irradiating intact skin tissue behind an irradiation window by directing electromagnetic excitation radiation from said radiation source to a portion of the outer skin surface behind the irradiation window; and
a detector for measuring an amount of electromagnetic fluorescent radiation emitted in response to said irradiation received simultaneously from only a portion of said irradiated skin surface portion; and
circuitry connected to said pick-up unit for generating an autofluorescence value for said non-locally anomalous, intact skin tissue in agreement with a measured amount of fluorescent radiation originating from said portion of said irradiated portion of said skin surface, for determining an advanced glycation/glycosylation end product content of said skin tissue from said signal, and for outputting said determined advanced glycation/glycosylation end product content.

15. An apparatus according to claim 14, wherein the detector is arranged for measuring electromagnetic fluorescent radiation received from a surface area of said portion of said irradiated skin surface portion of at least 1 cm$^2$.

16. An apparatus according to claim 14, wherein the surface area of the irradiated portion of the skin surface from which the fluorescent radiation emitted in response to said irradiation can be received simultaneously is larger than 0.1 cm$^2$.

17. A method for determining an advanced glycation/glycosylation end product content for a human individual, comprising:
    irradiating skin tissue of said individual with electromagnetic excitation radiation;
    receiving and measuring an amount of electromagnetic, fluorescent radiation emitted by said material in response to said irradiation; and
    generating, in response to said measured amount of fluorescent radiation, a signal which represents a determined advanced glycation/glycosylation end product content for said individual;
    wherein said skin tissue is non-locally anomalous, intact skin tissue in vivo of which a surface is irradiated non-invasively and simultaneously in its entirety;
    wherein fluorescent radiation emitted in a direction at an angle to the direction of the excitation radiation is simultaneously received from different portions of the skin surface;
    wherein said fluorescent radiation is received via a measuring window; and
    wherein said measuring window is oriented at an angle of 25-65° relative to the irradiated surface of the skin.

18. A method for determining an advanced glycation/glycosylation end product content for a human individual, comprising:
    irradiating skin tissue of said individual with electromagnetic excitation radiation via an opening in a surface contacting the skin;
    receiving and measuring an amount of electromagnetic, fluorescent radiation emitted by said material in response to said irradiation; and
    generating, in response to said measured amount of fluorescent radiation, a signal which represents a determined advanced glycation/glycosylation end product content for said individual;
    wherein said skin tissue is non-locally anomalous, intact skin tissue in vivo of which a surface is irradiated non-invasively and simultaneously in its entirety;
    wherein fluorescent radiation emitted in response to said irradiation is simultaneously received from different portions of the skin surface; and
    wherein said fluorescent radiation is received via a measuring window and wherein said measuring window is held at a distance from the skin.

19. An apparatus for determining an advanced glycation/glycosylation end product content for a human individual, comprising:
    a pick-up unit with:
        a radiation source, for in vivo and noninvasively irradiating a surface of non-locally anomalous, intact skin tissue with electromagnetic excitation radiation via an irradiation window for delimiting a surface portion of said skin tissue to be irradiated; and
        a detector for measuring an amount of electromagnetic fluorescent radiation received from a surface area of said skin tissue in a direction at an angle to the direction of the excitation radiation;
    circuitry connected to said pick-up unit for generating a value representing a determined advanced glycation/glycosylation end product content for said individual in agreement with the measured amount of fluorescent radiation originating from said surface area of said skin tissue; and
    a supporting structure to be held against the skin of the individual, for defining a plane in which a surface portion of said skin tissue to be irradiated is located;
    wherein the supporting structure supports a measuring window for passing light to be detected from said irradiated skin tissue, said measuring window being oriented at an angle of 25-65° relative to said plane.

20. An apparatus for determining an advanced glycation/glycosylation end product content for a human individual, comprising:
    a pick-up unit with:
        a radiation source, for in vivo and noninvasively irradiating a surface of non-locally anomalous, intact skin tissue behind an irradiation window with electromagnetic excitation radiation in a direction perpendicular to the skin; and
        a detector for measuring an amount of electromagnetic fluorescent radiation received from a surface area of said skin tissue;
    circuitry connected to said pick-up unit for generating a value representing a determined advanced glycation/glycosylation end product content for said individual in agreement with the measured amount of fluorescent radiation originating from said surface area of said skin tissue; and
    a supporting structure to be held against a skin of the individual, for defining a plane in which said surface of said skin tissue to be irradiated is located behind an opening in the supporting structure, wherein the supporting structure supports a measuring window for passing light to be detected coming from said irradiated skin tissue, wherein said measuring window is spaced away from said plane.

* * * * *

UNITED STATES PATENT AND TRADEMARK OFFICE
CERTIFICATE OF CORRECTION

PATENT NO. : 7,966,060 B2  
APPLICATION NO. : 10/767147  
DATED : June 21, 2011  
INVENTOR(S) : Andries Jan Smit et al.

Page 1 of 1

It is certified that error appears in the above-identified patent and that said Letters Patent is hereby corrected as shown below:

Column 11, line 29, "beheld" should read --be held--.

Signed and Sealed this
Sixteenth Day of August, 2011

David J. Kappos
*Director of the United States Patent and Trademark Office*